United States Patent [19]

Lohaus et al.

[11] 3,968,118

[45] July 6, 1976

[54] PROCESS FOR THE MANUFACTURE OF 1-HYDROXY-2-PYRIDONES

[75] Inventors: Gerhard Lohaus, Kelkheim, Taunus; Walter Dittmar, Hofheim, Taunus, both of Germany

[73] Assignee: Hoechst Aktiengesellschaft, Frankfurt am Main, Germany

[22] Filed: Aug. 30, 1974

[21] Appl. No.: 502,063

Related U.S. Application Data

[60] Division of Ser. No. 317,837, Nov. 22, 1972, Pat. No. 3,883,545, which is a continuation of Ser. No. 199,320, Nov. 16, 1971, abandoned, which is a continuation-in-part of Ser. No. 851,428, Aug. 19, 1969, abandoned.

[30] Foreign Application Priority Data

Aug. 31, 1968  Germany............................ 1795270

[52] U.S. Cl............................................. 260/297 Z
[51] Int. Cl.²....................................... C07D 213/02
[58] Field of Search................... 260/297 Z; 424/263

[56] References Cited
UNITED STATES PATENTS

| | | | |
|---|---|---|---|
| 2,540,218 | 2/1951 | Shaw................................ | 260/297 Z |
| 2,748,142 | 5/1956 | Clauson-Kaas et al.......... | 260/297 Z |
| 3,227,708 | 1/1966 | Yale et al. ....................... | 260/243 A |
| 3,269,904 | 8/1966 | Bernstein et al................. | 424/263 |
| 3,883,545 | 5/1975 | Lohaus et al..................... | 260/297 Z |

OTHER PUBLICATIONS
Adams et al., J. Am. Chem. Soc., vol. 81, pp. 2537–2541, (1959).

Klingsberg et al., Pyridine and Its Derivatives, Part 3, pp. 516–522, Interscience Publishers, (1962).

*Primary Examiner*—John D. Randolph
*Attorney, Agent, or Firm*—Curtis, Morris & Safford

[57] ABSTRACT

New 1-hydroxy-2-pyridones of the general formula

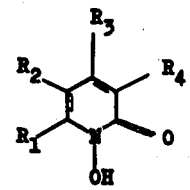

in which $R_1$ is alkyl of 1 to 17 carbon atoms, cycloalkyl of 5 to 8 carbon atoms, cyclohexylalkyl or phenalkyl both having 1 to 3 carbon atoms in the alkylene chain or α-furyl, all of which may be substituted by halogen, and $R_2$ to $R_4$ are hydrogen or lower alkyl, or two adjacent substituents together form a trimethylene or tetramethylene chain, and in which $R_1$ to $R_4$ together contain at least 2 carbon atoms, are prepared by contacting unsaturated δ-keto esters or mixtures thereof with hydroxylamine and subjecting the products to cyclization.

7 Claims, No Drawings

PROCESS FOR THE MANUFACTURE OF 1-HYDROXY-2-PYRIDONES

This application is a divisional of U.S. Pat. application Ser. No. 317,837 filed Dec. 22, 1972 (now U.S. Pat. No. 3,883,545 granted May 13, 1975), which in turn is a continuation of U.S. Pat. application Ser. No. 199,320 filed Nov. 16, 1971 (now abandoned), which in turn is a continuation-in-part of U.S. Pat. application Ser. No. 851,428, filed Aug. 19, 1969 (now abandoned).

This invention relates to certain 1-hydroxy-pyridones containing alkyl of 7 to 11 carbon atoms in the 6 position, and to a method for making substituted 1-hydroxy-pyridones.

The process for the manufacture of 1-hydroxy-pyridones of the general formula I

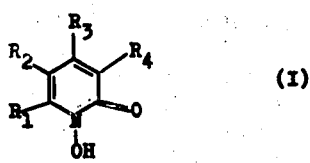

in which $R_1$ is alkyl of 1 to 17 carbon atoms, cycloalkyl of 5 to 7 carbon atoms, cyclohexylalkyl or phenalkyl both having 1 to 3 carbon atoms in the alkylene chain or α-furyl, all of which may be substituted by halogen, and $R_2$ to $R_4$ are hydrogen or lower alkyl or two adjacent substituents together form a trimethylene or tetramethylene chain, and in which $R_1$ to $R_4$ together contain at least 2 carbon atoms, comprises contacting unsaturated δ-keto-esters of the general formulae

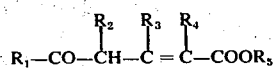

or

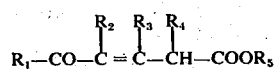

in which $R_1$ to $R_4$ have the meanings given above and $R_5$ represents a lower alkyl group, or mixtures thereof with hydroxylamine or its acid addition salts, and subjecting the products to cyclization in an acid or alkaline medium at temperatures of from 0° to 150°C.

Instead of free hydroxylamine or salts thereof, derivatives of hydroxylamine may be used, for example hydroxylaminesulfonic acids or oximes of lower aliphatic aldehydes or ketones.

The process of the invention may be varied within wide limits. For example, the reaction of unsaturated ketoesters to form the hydroxy-pyridones may be carried out in several steps, whereby the oxime esters obtained as intermediates are isolated; it may, however, also be carried out in a single step.

The oximes may, for example, be prepared in a buffered system by the reaction of hydroxylamine salts with ketoesters and subsequently ring closure may be effected in a stronger acid or alkaline medium.

The desired buffer effect may, for example, be attained by means of salts of weak or moderately strong acids, such as potassium formiate, sodium acetate, sodium phosphate, sodium carbonate, sodium bicarbonate, and sodium sulfite. By adding such salts the pH of the hydroxylamine salt solution can be adjusted close to the neutral point (about 5 to 8), thus accelerating the formation of oximes. In the course of oxime formation free acid is formed, the pH of the solution decreases and, below a pH of about 3 to 4, cyclization begins to take place at an appreciable speed to yield the hydroxy-pyridone. By adding inorganic or organic acids at this step, cyclization can be accelerated. If an alkaline catalysis is intended for cyclization, a pH above approximately 9.5 to 10 is advantageous in order to afford a satisfactory result within a reasonable reaction period.

It is also possible to prepare the hydroxy-pyridones directly in an unbuffered system by reacting keto-esters with hydroxylamine salts, if desired with the addition of mineral acids, such as hydrochloric acid, hydrobromic acid, sulfuric acid, nitric acid, phosphoric acid, perchloric acid, or strong organic acids, such as methanesulfonic acid, benzene-sulfonic acid, trichloracetic acid, dichloracetic acid, trifluoroacetic acid, oxalic acid or cyanacetic acid.

According to another method, formation of oximes and cyclization are effected by heating the reaction components in the presence of lower fatty acids, such as formic acid, acetic acid or propionic acid, whereby the alcoholic component of the keto-ester reacts with the fatty acid to form a readily volatile ester which is gradually separated by distillation.

It is also possible to use even higher fatty acids while optionally operating at reduced pressure for a better removal of the ester; this method, however, does generally not bring any advantage.

The reaction temperature is not critical for any of the methods described; it is, however, convenient to adapt it to the specific reaction conditions, for example to the necessary distillation of volatile components. As the examples will demonstrate, the hydroxy-pyridones can be prepared according to the process of the invention at 0°C as well as at 150°C.

In general, it can be said that cyclization proceeds at a higher speed under alkaline conditions than it does under acid conditions, for example to be more specific at a pH of 12 it proceeds more rapidly than at pH 10 or at pH 1 more rapidly than at pH 3. In a strongly alkaline medium, the conversion of the oxime ester into the hydroxy-pyridone may be complete at room temperature already within a few minutes or even seconds, whereas this reaction would require a couple of hours in an acid medium at room temperature. This is why it is advantageous under these conditions to choose higher reaction temperatures for the reason of saving time.

The choice of the possible embodiments of the invention depends on various factors; a decisive factor is, above all, the ease in working-up. If the compounds form sparingly soluble alkali metal salts, cyclization may advantageously be effected, for example by means of excess sodium hydroxide solution, and isolation of the reaction product as the sodium salt may be advantageous. If there is no such possibility, somewhat longer reaction times would be required under certain circumstances at a slightly reduced pH for saving neutralization of large amounts of alkali.

The same applies to the acid medium. Thus, some hydroxypyridones form, in concentrated hydrochloric acid, sparingly soluble hydrochlorides which can be filtered off; in the case of other compounds, the hydrochlorides and other salts with acids are easily soluble in water; in this case, only the isolation of the free hydroxy-pyridones by neutralization of at least part of the acid is taken into account.

The reaction may be carried out in the presence or absence of solvents, preferably polar solvents.

By solents there are to be understood adjuvants in which one or other or both reation components are, to a certain extent, soluble at the reaction temperature and which are inert toward the reation components. They may be miscible with water or not.

Suitable slvents are, for example, water; lower alcohols, such as methanol, ethanol, propanol, isopropanol, butanols, ethylene-glycol, 1,2-propylene-glycol, 1,3-propylene-glycol, glycerol, ethylene-glycol monomethyl ether, ethylene-glycol monoethyl ether, ethers, such as tetrahydrofuran, dioxan, ethylene-glycol dimethyl ether; nitro compounds, such as nitro-methane, nitro-ethane, 2-nitro-propane, nitrobenzene; nitriles, such as acetonitrile, propionitrile, benzonitrile. Aromatic compounds, such as benzene, toluene, xylene, chlorobenzene, dichlorobenzene, chloro-toluene, anisole, phenol, benzyl alcohol, benzoic acid methyl ester, or lower carboxylic acids, such as formic acid, acetic acid, propionic acid, butyric acid, isobutyric acid, chloracetic acid, dichloracetic acid, glycolic acid, diethyl-formamide, acid; acid amides, such as formamide, monomethyl-formamide, dimethyl-formamide, diethylformamide, dimethyl-acetamide, pyrrolidone, N-methyl-pyrrolidone, dimethylsulfoxide, or tetramethylene-sulfone may also be used.

The δ-keto-esters used as starting material can be obtained in an especially advantageous manner by condensation of carboxylic acid chlorides with β,β-dialkyl-acrylic esters in the presence of Friedel-Crafts catalysts, as described in Belgian Pat. No. 637 170.

Compounds that can be prepared by the process of the invention are, for example, the following:
1-hydroxy-4,6-dimethyl-2-pyridone,
1-hydroxy-3,4,6-trimethyl-2-pyridone,
1-hydroxy-4-methyl-6-ethyl-2-pyridone,
1-hydroxy-4,6-dimethyl-5-ethyl-2-pyridone,
1-hydroxy:4-ethyl-5,6-dimethyl-2l -pyridone,
1-hydroxy-3-ethyl-4-methyl-6-isobutyl-2l -pyridone,
1-hydroxy-4-methyl-6-cyclohexyl-2-pyridone,
1-hydroxy-4-methyl-6-cyclohexylmethyl-2-pyridone,
1-hydroxy-4-methyl-6-(β-cyclohexylethyl)-2-pyridone,
1-hydroxy-3,4-dimethyl-6-cyclopentyl-2-pyridone,
1-hydroxy-4-methyl-6-chloromethyl-2-pyridone,
1-hydroxy-4-methyl-6-(β-chloroethyl)-2-pyridone,
1-hydroxy-4-methyl-6-bromomethyl-2-pyridone,
1-hydroxy-4-methyl-6-isopropyl-2-pyridone,
1-hydroxy-3,6-dibutyl-4-methyl-2-pyridone,
1-hydroxy-4-methyl-6-heptyl-2-pyridone,
1-hydroxy-[4-methyl-6-undecyl-2-pyridone,
1-hydroxy-3,4-dimethyl-6-benzyl-2-pyridone,
1-hydroxy-4-methyl-6-(4-chlorobenzyl)-2-pyridone,
1-hydroxy-4,5-trimethylene-6-methyl-2-pyridone,
1-hydroxy-4-methyl-6-(α-furyl)-2-pyridone,
1-hydroxy-3,4-dimethyl-6-(4-fluorobenzyl)-2-pyridone.

According to Chem. Abstr. 55, page 24,742 (1961), 1-hydroxy-pyridones which are unsubstituted or substituted by a methyl group in 4 or 6 position are known. According to U.S. Pat. No. 3,269,904 and J. Am. Chem. Soc. 81, page 2537 (1959), hydroxy-pyridine-1-oxides containing methyl groups in 4 or 6 position may be obtained by alkaline hydrolysis of the corresponding 2-halogeno-pyridine-oxides.

The cyclization method according to the invention is novel and surprising. The unsaturated δ-keto-esters used as starting material may be meant as α,β-unsaturated ketones or as α,β-unsaturated carboxylic acid esters.

It is known that the reaction of α,β-unsaturated ketones with hydroxylamine, in many cases, leads to five-membered heterocyclic rings in which the oxygen atom of the hydroxylamine is incorporated, namely $\Delta^2$- and $\Delta^4$-isoxazolines (for instance, Elderfield, Heterocyclic Compounds, Vol. 5, pages 476 et seq., John Wiley & Sons, New York, 1957; F. Stockhausen and L. Gettermann, Ber. dtsch. chem. Ges. 25, p. 3535 (1892)).

Addition reactions of hydroxylamine with the double bond of α,β-unsaturated ketones, in which the carbonyl group may even be unaltered, are also known [cf. for instance, C. Harries and F. Lehmann, Ber. dtsch. chem. Ges. 30, p. 230,2726 (1897)].

Analogous reactions would have also to be expected for the reaction of the invention.

It is also known that α,β-unsaturated carboxylic acid esters easily cause hydroxylamine to enter into an addition reaction with the double bond, moreover the ester function can be converted into a hydroxamic acid. These reactions may proceed simultaneously so that, under certain circumstances, a complex reaction procedure is observed [cf. C. Harries and W. Haarmann, Ber. dtsch. chem. Ges. 37, p. 252 (1904); T. Posner, Ber. dtsch. chem. Ges. 40, p. 222 (1907)]. The reaction of α,β-unsaturated carboxylic acid esters yielding isoxazolones while incorporating the oxygen atom of the hydroxylamine, is also known [cf. A. Tingle, Am. Chem. J. 24, p. 50 (1900)].

Compounds which simultaneously carry an ester and a keto function in the molecule, such as β-keto-carboxylic acid esters, react in the same manner as the unsaturated ketones while incorporating the oxygen atom of the hydroxylamine, to yield 5-membered heterocyclic rings, namely the isoxazolones or even the dimeric isoxazolones [cf. A. Hantzsch, Ber. dtsch. chem. Ges. 24, p. 502 (1891)].

Finally, the reaction of compounds which carry, in the molecule, both the ester and keto functions and a double bond, with hydroxylamine is known. The benzalacetoacetic ester yields an isoxazolone derivative [cf. E. Knoevennagel and W. Renner, Ber. dtsch. Chem. Ges. 28, p. 2994 (1895)].

The cyclization reaction of the invention could therefore not be foreseen.

Moreover, the process of the invention is an especially smooth and simple method for making substituted hydroxy-pyridones and can, in addition, be applied for a variety of compounds since the aliphatic starting substances can easily be obtained. The hitherto known 1-hydroxy-pyridones have, however, always been obtained from heterocyclic compounds, among which only those derivatives which carry lower substituents are easily available.

The compounds obtainable by the process of the invention have good antimycotic properties and are therefore useful medicaments against dermatomycoses. In vitro, they are effective not only against usual dermatophytes (trichophyton and microsporum species) and against Candida albicans but also against the more dangerous pathogens, for example Cryptococcus neoformans, Blastomyces dermatitidis, Nocardia asteroides, Dermatophilus congolense, furthermore Aspergillus fumigatus and other molds, for example Mucor miehei, Absidia corymbifera, Aspergillus niger.

As to their antimycotic in-vivo properties, the compounds of claim 2 are substantially superior to the hydroxy-pyridones carrying only one methyl group in 4 or 6 position, for example known from U.S. Pat. No. 3,269,904. The compounds of the invention have been tested in vitro and in vivo as to their antimycotic properties and have been compared with the above-mentioned known compounds which are either unsubstituted or are substituted by methyl in 4 or 6 position:

A. 1-hydroxy-2-pyridone,
B. 1-hydroxy-4-methyl-2-pyridone,
C. 1-hydroxy-6-methyl-2-pyridone,
D. 1-hydroxy-4-methyl-6-heptyl-2-pyridone, (claim 3 of this application)
E. 1-hydroxy-4-methyl-6-undecyl-2-pyridone (claim 4 of this application)

Contents: neopeptone 1 gram, glucose 2 grams, made up to 100 ml with distilled water, pH adjusted to 6.5 (NaOH).

Germs: As representative types of fungi there were used (cf. column 2):

1. Trichophyton mentagrophytes (109)
2. Microsporum canis (559)
3. Candida albicans (St 1)
4. " " (H29)
5. Aspergillus niger (533)
6. " fumigatus (A1)

Preliminary cultivation:

1.,2.,5.,6.: 4 weeks/28°C/malt extract-dextrosepeptone agar,
3.,4.: 2 weeks, further conditions as above.

Inoculum:

1.,2.,5.,6.: 1 × $10^6$ microconidia resp.spores/ml, (final conc.) 3.,4.: 1 × $10^5$ yeast cells/ml.

Readings of the fungistatic concentrations of the preparation: after 10 days of cultivation at 28°C.

Table

| Compound | Pathogen type | MIC. mcg./ml. |
|---|---|---|
| A | 1 | 62.5 |
| A | 2 | >125 |
| A | 3 | >125 |
| A | 4 | >125 |
| A | 5 | >125 |
| A | 6 | >125 |
| B | 1 | 31.3 |
| B | 2 | 125 |
| B | 3 | >125 |
| B | 4 | >125 |
| B | 5 | >125 |
| B | 6 | >125 |
| C | 1 | 15.6 |
| C | 2 | 62.5 |
| C | 3 | 125 |
| C | 4 | 125 |
| C | 5 | 125 |
| C | 6 | 62.5 |
| D | 1 | 15.6 |
| D | 2 | 15.6 |
| D | 3 | 15.6 |
| D | 4 | 7.8 |
| D | 5 | 15.6 |
| D | 6 | 15.6 |
| E | 1 | 15.6 |
| E | 2 | 15.6 |
| E | 3 | 15.6 |
| E | 4 | 7.8 |
| E | 5 | 15.6 |
| E | 6 | 15.6 |

The results obtained are compiled in Table 1, column 2 indicating the pathogenic type of fungi and column 3 the concentration in microgram/milliliter of medium, required to inhibit growth (MIC = Minimum Inhibitory Concentration). Column 4 is a graphic diagram of the figures given in column 3.

Testing method

Dilution series were made from the compounds in Sabouraud's liquid medium at pH 6.5. No growth-inhibiting concentrations of solvents were contained (maximum 2% of methanol).

Tested concentrations : 125 to 0.25 mcg/ml.
Test medium

Difco-Sabouraud medium ready for use, article 0382-01 (Contr. 548294).

the results compiled in the Table demonstrate that the compounds D and E of the invention in which the substituent in 6 position is an alkyl group having 7 or 11 carbon atoms have, on an average, at least 4 times the fungistatic activity in vitro of the known compounds A to C which are unsubstituted or substituted by a methyl group in 4 or 6 position. In the case of the especially important germ Candida Albicans, the novel compounds have an 8- to 16-fold improved activity. Even in vivo, upon a test infection of the Guinea pig with dermatophytes, the 6-heptyl- and 6-undecyl-4-methyl-1-hydroxy-2-pyridones C and D have an about 3 times higher antimycotic activity upon local administration than the known compounds. The compounds of Claims 2 to 4 have a broadspectrum antimycotic nature so that they can be used in general against the most important superficial fungal diseases of human beings, if desired without being combind with other antimicrobial compounds.

The compounds can be administered in the free or salt form, especially as salts with physiologically acceptable alkaline compounds. They are administered in the form of solutions, for example in alcohols or polyglycols, creams, ointments, powders or sprays, which are applid superficially to the affected areas of the skin. As carrier substances suitable for the pharmaceutical compositions there are used therapeutically useful substances, for example paraffins, vaseline or lanoline for the ointments and talc for the powders. The percentage of active ingredient is between 0.2 and 2% for solutions and semi-solid compositions.

The following Examples serve to illustrate the invention, but they are not intended to limit it thereto.

EXAMPLE 1

740 g of hydroxylamine-hydrochloride, 750 g of sodium formiate and 1,495 g of a mixture of 5-oxo-3-methylhexene-(2)-acid-(1)-methyl ester and 5-oxo-3-methyl-hexene-(3)-acid-(1)-methyl ester, which mixture had been obtained by condensation of acetylchloride with $\beta,\beta$-dimethyl-acrylic acid methyl ester, in 1,500 ml of formic acid were heated to 110° to 130°C, whereupon the formic acid methyl ester formed distilled off via a column. Subsequently, the majority of the formic acid was distilled off, ice was added to the residue, the precipitated 1-hydroxy-4,6-dimethyl-2-pyridone was suction-filtered and washed with cold water. The yield of the compound melting at 135°C was 571 grams. Another 59 g could be obtained from the mother liquor. The structure of the substance resulted from the elementary analysis:
(calculated: 60.5% C, 6.5% H, 10.0% N;
found: 60.8% C, 6.8% H, 10.0% N) and from its splitting by boiling it with Raney-nickel in ethanol to form 4,6-dimethyl-2-pyridone known from the literature.

Analogous results were obtained using acetic acid or propionic acid instead of formic acid and sodium acetate or sodium propionate instead of sodium formiate.

EXAMPLE 2

19.8 g of 5-oxo-3-methyl-hexene-(3)-acid-(1)-isobutyl ester in a solution of 9 g of hydroxylamine-sulfate and 3 ml of concentrated sulfuric acid in 30 ml of water were heated to 100°C for 2 hours. After cooling the pH of the solution was adjusted to 4 by means of sodium carbonate, whereupon 5.15 g of 1-hydroxy-4,6-dimethyl-2-pyridone crystallized. Another 1.7 g of the same product could be obtained by extraction of the solution by means of methylene chloride.

EXAMPLE 3

78 g of the ester mixture used in Example 1 and 50 ml of methanol were added to a solution of 40 g of hydroxylaminehydrochloride and 26 g of sodium carbonate in 150 ml of water and the mixture was stirred for 5 hours at room temperature. The mixture was then shaken with methylene chloride, the organic phase was washed with water and distilled. 76.5 g of the mixture of isomeric oxime esters were obtained having a boiling point of from 90° to 110°C under a pressure of 0.1 torr. (Calculated: 56.2% C, 7.7% H, 8.2% N, 18.1% $OCH_3$; found: 56.2% C, 7.8% H, 8.3% N, 17.7% $OCH_3$).

17.1 g of the distillate and 15 ml of glacial acetic acid were heated for 1 hour at a bath temperature of 140°C and the methylacetate formed was distilled off. The residue was placed on ice, whereupon 5.8 g of 1-hydroxy-4,6-dimethyl-2-pyridone crystallized.

EXAMPLE 4

15.6 g of the ester mixture used in Example 1, 8 g of hydroxylamine-hydrochloride and 9.4 g of sodium acetate were stirred for 24 hours at 0°C in a mixture of 15 ml of methanol and 15 ml of water. At the same temperature, a solution of 6 g of sodium hydroxide in 12 ml of water was then added, the whole was stirred for 1 hour, acidified to reach a pH of 4 and the methanol was distilled off in vacuo. From the residue 3.5 g of 1-hydroxy-4,6-dimethyl-2-pyridone crystallized.

EXAMPLE 5 a. 15.6g of the ester mixture used in Example 1 and a solution of 8 g of hydroxylamine-hydrochloride in 25 ml of water were shaken at 25°C, whereupon, after about 4 hours, a homogeneous solution was obtained. After 48 hours the pH-value of the solution was adjusted to 4 by means of sodium carbonate and the precipitated 1-hydroxy-4,6-dimethyl-2-pyridone was suction-filtered. The yield was 4.6 grams.

b. Under the same reaction conditions, from 5-oxo-hexene-(2)-acid-(1)-ethyl ester 1-hydroxy-6-methyl-2-pyridone having a melting point of 141°C which is known from the literature was obtained.

c. From 6-chloro-5-oxo-3-methyl-hexene-(2)-acid-(1)-methyl ester 1-hydroxy-4-methyl-6-chloromethyl-2-pyridone, melting point 196°C, was obtained. (Calculated: 48.5% C, 4.6% H, 8.1% N, 20.4% Cl; found: 48.7% C, 4.7% H, 8.2% N, 20.2% Cl) and d. from 5-oxo-2,3-dimethyl-hexene-(2)-acid-(1)-ethyl ester 1-hydroxy-3,4,6-trimethyl-2-pyridone, melting point 130°C, was obtained. (Calculated: 62.7% C, 7.2% H, 9.2% N; found: 62.7% C, 7.1% H, 9.3% N).

EXAMPLE 6 a. 11.2 g of a mixture of 5-oxo-3-methyl-5-cyclohexylpentene-(2)-acid-(1)-methyl ester and 5-oxo-3-methyl-cyclohexyl-pentene-(3)-acid-(1)-methyl ester, which mixture had been obtained by condensation of hexahydrobenzoyl-chloride with $\beta,\beta$-dimethyl-acrylic acid methyl ester, and a solution of 4.6 g of sodium acetate and 4 g of hydroxylamine-hydrochloride were shaken for 20 hours at 25°C with a mixture of 8 ml of water and 15 ml of methanol. Subsequently, a solution of 4 g of sodium hydroxide in 8 ml of water was then added, while cooling, shaken for another hour at room temperature, extracted by means of benzene and the aqueous phase was acidified to reach a pH-value of 6. 3.5 g of 1-hydroxy-4-methyl-6-cyclohexyl-2-pyridone, melting point 144°C, were obtained (Calculated: 69.5% C, 8.3% H, 6.8% N; found: 69.2% C, 8.3% H, 6.8% N).

Under the same conditions there were obtained b. from 5-oxo-3-methyl-dodecene-(2)-acid-(1)-methylester 1-hydroxy-4-methyl-6-n-heptyl-2-pyridone, melting point 48°C, (calculated 69.9% C, 9.5% H, 6.3% N; found: 70.0% C, 9.5% H, 6.2% N), c. from 5-oxo-3-oxo-3-ethyl-4-methyl-hexene-(3)-acid-(1)-methyl ester 1-hydroxy-4-ethyl-5,6-dimethyl-2-pyridone, melting point 138°C, (calculated: 64.7% C, 7.8% H, 8.4% N; found: 64.9% C, 7.8% H, 8.6% N), d. from 2-acetyl-cyclopentene-1-acetic acid methyl ester 1-hydroxy-4,5-trimethylene-6-methyl-2-pyridone, melting point 178°C (calculated: 65.4% C, 6.7% H, 8.5% N; found: 65.3% C, 6.9% H, 8.4% N), e. from 5-oxo-3-methyl-6-(4-chlorophenyl)-hexene-(2)-acid-(1)-methyl ester, 1-hydroxy-4-methyl-6-(4-chlorobenzyl)-2-pyridone, melting point 141°C (calculated: 62.5% C, 4.9% H, 5.6% N, 14.2% Cl; found: 62.3% C, 5.0% H, 5.9% N, 14.4% Cl), f. from 5-oxo-3-methyl-6-cyclohexyl-hexene-(2)-acid-(1)methyl ester 1-hydroxy-4-methyl-6-cyclohexylmethyl-2-pyridone, melting point 131°C (calculated: 70.5% C, 8.7% H, 6.3% N; found: 70.2% C, 8.7% H, 6.5% N) and g. from 5-oxo-3-methyl-7-cyclohexyl-heptent-(2)-acid-(1)methyl ester 1-hydroxy-4-methyl-6-($\beta$-cyclohexyl-ethyl)-2-pyridone, melting point 90°C (calculated: 71.4% C, 9.0% H, 6.0% N; found: 71.6% C, 8.7% H, 5.8% N).

EXAMPLE 7

8.5 g of 5-oxo-3-methyl-heptene-(2)-acid-(1)-methyl ester and a solution of 3.85 g of hydroxylamine-hydrochloride and 4.5 g of sodium acetate in 12 ml of water were shaken for 15 hours at room temperature. Subsequently a solution of 4 g of sodium hydroxide in 8 ml of water was added thereto, the mixture was cooled to 0°C after standing for 30 minutes at room temperature, the precipitated sodium salt of hydroxypyridone was suction-filtered, dissolved in water and free 1-hydroxy-4-methyl-6-ethyl-2-pyridone was precipitated by acidification at pH 5. The yield was 2.9 g of a compound that melted at 110°C.

Calculated: 62.7% C, 7.2% H, 9.2% N; Found: 62.7% C, 7.2% H, 9.4% N.

EXAMPLE 8

To a solution of 9.85 of hydroxylamine-hydrochloride and 8 g of tertiary sodium phosphate in 30 ml of water, 20 ml of methanol and 20 g of a mixture of 5-oxo-3,6-dimethylheptene-(2)-acid-(1)-methylester and 5-oxo-3,6-dimethylheptene-(3)-acid-(1)-methylester, which mixture had been obtained by condensation of isobutyric acid chloride with $\beta,\beta$-dimethylacrylic acid methyl ester, were added and the whole was shaken for 15 hours at room temperature. Subsequently a solution of 14 g of sodium hydroxide in 30 ml of water was added thereto, after having been shaken for 1 hour at room temperature the pH-value of the solution was adjusted to 5 by acidification and the 1-hydroxy-4-methyl-6-isopropyl-2-pyridone was shaken with methylene chloride. 5.6 g of a substance melting at 110°C was obtained.

Calculated: 64.6% C, 7.9% H, 8.4% N; found: 64.6% C, 8.0% H, 8.2% N.

EXAMPLE 9

A solution of 260 g of the ester mixture used in Example 1 in 220 ml of methylene chloride was added dropwise within 30 minutes to a boiling solution of 139 g of hydroxylaminehydrochloride in a mixture of 500 ml of water and 50 ml of concentrated hydrochloric acid, whereupon the methylene chloride distilled off. The mixture was heated to 100°C for another hour, subsequently adjusted to pH 4 by means of a sodium hydroxide solution, cooled to 0°C, the precipitate was suction-filtered and washed free from salt with cold water. 110 g of 1-hydroxy-4,6-dimethyl-2-pyridone were obtained.

EXAMPLE 10

A solution of 260 g of the ester mixture used in Example 1 in 250 ml of chlorobenzene and 115 g of pulverized hydroxylamine-hydrochloride were heated while stirring to 100°C for 4 hours. Subsequently the mixture was cooled to room temperature and the precipitated 1-hydroxy-4,6-dimethyl-2-pyridone was suction-filtered in a yield of 101 g. By dissolution in water and adjusting to a pH of 4, the free hydroxy-pyridone could be obtained therefrom.

EXAMPLE 11

18.3 g of acetone-oxime were dissolved in 39 g of the ester mixture used in Example 1, 5 ml of 1N-hydrochloric acid were added thereto and the whole was heated to 150°C in the oil bath. Via a column, methanol and acetone which had been set free were distilled off, heating at 150°C was continued for another 2 hours and the solution was then distilled in vacuo.

From the fraction that passed over at 120°–150°C under a pressure of 7 torr, 13.4 g of 1-hydroxy-4,6-dimethyl-2-pyridone, melting point 135°C, crystallized upon cooling.

EXAMPLE 12

8 g of hydroxylamine-hydrochloride were dissolved in 100 ml of methanol, 10 g of anhydrous sodium acetate and 22.4 g of a mixture of 5-oxo-3-methyl-5-cyclohexyl-pentene-(2)-acid-(1)-methyl ester and 5-oxo-3-methyl-5-cyclohexyl-pentene(3)-acid-(1)-methyl ester were added thereto and the whole was stirred for 20 hours at 0°C. Subsequently a solution of 10 g of sodium hydroxide in 15 ml of water was added and stirring was continued for another 10 hours at 0°C. Most of the methanol was distilled off in vacuo, the residue was taken up in 100 ml of water, extracted with methylene chloride, the pH of the solution was adjusted to 2 by acidification, the solution was shaken once more with methylene chloride, the acid extract obtained was concentrated in vacuo and 50 ml of concentrated hydrochloric acid were added thereto. The hydrochloride of 1-hydroxy-4-methyl-6-cyclohexyl-2-pyridone crystallized, it was suction-filtered, washed with concentrated hydrochloric acid and converted into the free hydroxypyridone by trituration with 100 ml of water.

EXAMPLE 13

52 g of a mixture of 5-oxo-3-methyl-5-($\alpha$-furyl)-pentene(2)-acid-(1)-methyl ester and 5-oxo-3-methyl-5-($\alpha$-furyl)-pentene-(3)-acid-(1)-methyl ester, which mixture had been obtained by condensation of pyromucic acid chloride with $\beta,\beta$-dimethylacrylic acid methyl ester, were heated to 80°C for 6 hours with 20 g of hydroxylamine-hydrochloride, 20 of sodium formiate and 75 ml of formic acid. Subsequently the formic acid was distilled off in vacuo, water was added to the residue and the mixture was shaken three times with 25 ml each of methylene chloride. The combined organic phases were washed with 25 ml of water, then shaken with a solution of 5 g of sodium carbonate in 30 ml of water and finally cooled to 0°C. 3.2 g of the sodium salt crystallized, were dissolved in water and acidified to form the free 1-hydroxy-4-methyl-6-(α-furyl)-2-pyridone having a melting point of 146°C.
Calculated:62.8% C, 4.8% H, 7.3% N
Found:63.0% C, 4.7% H, 7.4% N.

EXAMPLE 14

15.6 g of sodium acetate and 47.7 g of the unsaturated keto ester obtained from lauric acid chloride and dimethylacrylic acid methyl ester were added to a solution of 12.6 g of hydroxylamine-hydrochloride in 125 ml of methanol. The mixture was stirred for 20 hours at 0°C. A solution of 15.8 g of sodium hydroxide in 25 ml of water was then added, stirring was continued for two hours at room temperature, the solvent was separated by distillation in vacuo, the residue was dissolved in water, the solution was once shaken wih isopropyl ether, the aqueous solution was neutralized with carbon dioxide, shaken with methylene chloride and the organic phase was distilled. The main fraction boiled at 150°–190°C under a pressure of 0.1 torr and had a weight of 17.1 g. By diluting with hexane and cooling to −70°C 4.8 g of 1-hydroxy-4-methyl-6-undecyl-2-pyridone were obtained therefrom, m.p. 63°C. (Calculated: 73.1% C, 10.5% H; found: 72.9% C and 10.7% of H).

EXAMPLE 15

15.6 g of the ester mixture used in Example 1 were added to a solution of 6.95 of hydroxylamine-hydrochloride and 8.2g of anhydrous sodium acetate in 30 ml of water (pH 5.6) and the mixture was refluxed for 8 hours.

Subsequently, the mixture was cooled to 0°C, 50 ml of diisopropyl ether were added, the mixture was suction-filtered and washed with cold diisopropyl ether and water. Yield: 2.4 g of hydroxy-pyridone, m.p. 135°C. The pH of the aqueous phase was 3.4 at the end of the reaction.

When under the same conditions 8.4 g of potassium formiate were used instead of sodium acetate, the pH of the aqueous solution was 5.2 prior to the reaction and 1.6 after the reaction, and the yield of hydroxy-pyridone was 5.0 grams.

EXAMPLE 16

48 g of anhydrous sodium acetate and 112 g of the keto ester mixture used in Example 6 were added to a solution of 40 g of hydroxylamine-hydrochloride in a mixture of 50 ml of water and 250 ml of methanol. After the mixture had been shaken for 5 hours at room temperature, 30 ml of water were added, the n ture was cooled to −20°C, suction-filtered and sodium chloride which had precipitated was dissolved by subsequently washing with water. 19.2 g of the oxime of 5-oxo-3-methyl-5-cyclohexyl-pentene-(2)-oic acid-(1) methyl ester were obtained, m.p. 137°C. (Calc. 6 .3% of C, 8.8% of H and 5.9% of N, found: 65.2% C, 8.9% of H and 6.0% of N).

2.39 g of finely powdered oxime ester were h ted with a solution of 1.5 g of sodium carbonate in 5 ml of water and 20 ml of methanol (pH 10.9) to 90° for 3 minutes while carefully stirring.

In the course of this operation the product dissolved completely. At the end of the reaction the pH of th solution was 9.1. The solution was acidified, cooled in ice, suctionfiltered, the residue was washed with water and dried. The yield of hydroxy-pyridone was 1.88 grams.

We claim:

1. The method of making a 1-hydroxy-2-pyridone of the formula

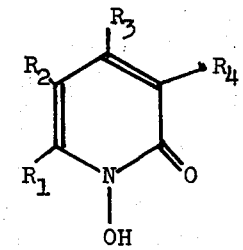

wherein $R_1$ is alkyl having 1 to 17 carbon atoms, cycloalkyl having 5 to 8 carbon atoms, α-furyl, or cyclohexylalkyl or phenylalkyl each having 1 to 3 carbon atoms in the alkyl portion thereof, all of which may be substituted by halogen; $R_2$ to $R_4$ are hydrogen or lower alkyl, or two adjacent substituents taken together form a trimethylene or tetramethylene chain; and $R_1$ to $R_4$ all together contain at least two carbon atoms, which method comprises reacting, at a temperature from 0° to 150°C., at least one unsaturated δ-keto ester of the formula

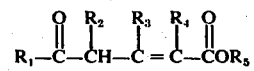

or defined

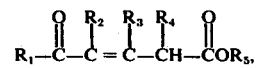

wherein $R_1$ to $R_4$ are as earlier defined and $R_5$ is lower alkyl, with hydroxylamine or an acid addition salt thereof.

2. The method as in claim 1 wherein the reaction occurs in the additional presence of an acid.

3. The method as in claim 2 wherein said acid is a mineral acid.

4. The method as in claim 2 wherein said acid is a lower fatty acid.

5. The method as in claim 1 wherein said reaction occurs in the additional presence of a buffer initially establishing a pH of about 5 to 8.

6. The method as in claim 5 wherein, after the establishment of a pH of about 3 to 4 in the reaction mixture by the production of acid during the formation of an intermediate oxime ester product, said oxime ester intermediate is subsequently cyclized by reducing pH to a value below about 3 to 4.

7. The method as in claim 5 wherein, after the establishment of a pH of about 3 to 4 in the reaction mixture by the production of acid during the formation of an intermediate oxime ester product, said oxime ester intermediate is subsequently cyclized by increasing pH to a value above about 9.5 to 10.

* * * * *